United States Patent [19]

Smith

[11] Patent Number: 4,566,449

[45] Date of Patent: Jan. 28, 1986

[54] ELEVATED INFANT POSITIONER

[76] Inventor: Jan E. Smith, 6936 Garden Grove Ave., Reseda, Calif. 91335

[21] Appl. No.: 547,009

[22] Filed: Oct. 31, 1983

[51] Int. Cl.⁴ ............................................. A61F 13/00
[52] U.S. Cl. .................................................. 128/133
[58] Field of Search ............................ 5/431; 128/133

[56] References Cited

U.S. PATENT DOCUMENTS

| | | | |
|---|---|---|---|
| 2,281,629 | 5/1942 | Snow | 5/431 |
| 3,284,817 | 11/1966 | Landwirth | 5/431 |
| 4,048,681 | 9/1977 | Baulch et al. | 5/431 |
| 4,383,713 | 5/1983 | Roston | 5/431 |
| 4,441,221 | 4/1984 | Enste et al. | 5/431 |

*Primary Examiner*—John D. Yasko
*Assistant Examiner*—Christa K. Scott
*Attorney, Agent, or Firm*—Singer & Singer

[57] ABSTRACT

A positioner for holding and supporting an infant in either a prone or supine position consisting of a wedge having a first plane at a given angle of at least 30 degrees that is contiguous with a second plane having an angle that is less than the angle of the first plane. A bifurcated U-shaped member is located over the first plane and the extending tapered arms of the bifurcated U-shaped member contact both portions of the first plane and the second plane thereby preventing movement of the infant in a vertical direction or in a lateral direction while at the same time allowing the infant to move in a safe and unrestrained manner.

12 Claims, 6 Drawing Figures

ELEVATED INFANT POSITIONER

This invention relates to a device for positioning an infant in either a prone or supine position and more particularly to a device that is capable of safely holding and positioning an infant and one that is capable of being used by both lay people and professionals.

The medical literature is primarily concerned with the handling of newborn infants and especially premature infants that are typically less than five pounds.

Chronically ill infants or premature infants have a tendency to regurgitate their feedings which is believed caused by two physiological mechanisms. An infant in an unsupported position has pressure on the diaphragm which is pushed on by other internal organs. This pressure can cause the stomach contents to be forced into the esophagus and possibly into the lungs because of an immature nerve mechanism controlling the esophageal sphincter. When this happens in the premature infant the result can be physical damage and even death.

The medical term used to define this activity is called Gastroesophageal Reflux which is technically defined as a dysfunction of the distal esophagus causing frequent return of stomach contents into the esophagus and is frequently associated with vomiting. Current medical thinking indicates that the problem is more severe in premature infants because of the inability of the infant to cough or otherwise involuntarily clear the lungs and assure a free passage of air.

The premature infant is particularly susceptible to this damaging activity because of the incomplete development of the nerve endings and the fact that the reflex action is not completely developed, thereby depriving the infant of the lifesaving ability to develop a reflex coughing action. This action must await the more complete development of the nerve endings of the infant and the passage of time.

Medical authorities all seem to agree that the infant must be positioned in a more vertical position in either a supine or prone position for at least six weeks to six months as the infant develops and grows. The authorities do not generally agree on which position is best, however, the authorities do agree that a more vertical position of at least 30 degrees is not only necessary but essential if the child is to live past the critical time.

Prior art devices have included such diverse techniques as strapping the infant to a plywood board maintained at some given angle or placing the infant in a bassinet maintained at a given angle with straps to prevent the infant from falling out. These prior art devices have not been successful because they limit the child's movement and hence hinder the development of the child during its normally active and growing time up to the time of six months.

The prior art describes the problem as exemplified by an article entitled Medical Progress—Gastroesophageal Reflux by John J. Herbst, M.D., Salt Lake City, Utah, and printed in the Journal of Pediatrics, June 1981. The article describes the problem of the newborn infant and FIG. 3 in the article illustrates a padded peg or saddle to maintain the child on the inclined plane and with straps to keep the child from falling off the board.

The problem of maintaining and positioning the child at home by the layman is more fully set forth in an article by Carol Wentz Boyd, RN, MSN, entitled Postural Therapy at Home for Infants with Gastroesophageal Reflux which appeared in the November-December 1982 issue of a magazine entitled Pediatric Nursing.

This article is directed more to the problem of the laymen who are advised that the child must be maintained in this vertical position for six months and that it is fatal to allow the child to become horizontal even for a short period of time. The emotional problems suffered by the parents are fully explained and certain makeshift ways including beach towels and special beds are described. The problem is particularly acute when it is recognized that the infant must not only be maintained in this vertical position during sleeping and waking, but also during feeding, washing and diaper changes. The article strongly suggests that when bathing the infant that an angle of even 60 degrees should be maintained. The Boyd article further describes how infant equipment such as an infant seat or car seat or special bed can be adapted to maintain the infant in a more horizontal position.

A review of the Patent Office records discloses only certain therapeutic devices for supporting the infant in either one position or in a second position and for a temporary period of time. For example, U.S. Pat. No. 2,281,629 entitled Device for Preventing Colic in Feeding Infants illustrates a contoured cushion for holding a child in a supine position. Unfortunately the cushion is only useful for a supine position and requires the child to be strapped in, thereby preventing normal movement and development of the child during times other than for feeding.

U.S. Pat. No. 3,555,582 entitled Therapeutic Device issued to W. S. Radford describes a cushion having certain curves which are claimed to have some therapeutic value to the user. Unfortunately the cushion contains no means of supporting an infant in either the vertical position or to prevent movement of the infant in a lateral position and otherwise simply shows that an incline plane in the form of a cushion has been used and for different reasons.

While the current medical opinion requires the newborn infant to be maintained in a more vertical position, there is nothing available that can safely support the infant in either a prone or supine position and at the same time allow the infant to move and provide lateral support for safety purposes.

The present invention enables chronically ill infants to be safely positioned either prone or supine and in a manner that minimizes the regurgitation problems described. In addition, the present invention also promotes normal development of the gross motor skills of the infant which apparently seem to be lacking possibly because of the limitations of the currently available positioners. Further, it is also important to notice that the infant is now able to develop the upper trunk muscles while maintaining an elevated position.

In the broadest concept the present invention comprises a molded foam wedge having a first plane for supporting the infant's body. Each side of the wedge is contoured so that the infant may lie either on his back or his stomach with the wedge keeping him in an elevated position. If it is desired, the infant may be restrained by means of Velcro straps attached to the clothing of the infant or to restraints attached to the wedge itself.

The wedge is designed to include a second plane having an angle that is less than the angle of the first plane and that is contiguous with the first plane and with the buttocks of the infant resting in the molded contour. The second plane is at an angled position so that the head and upper trunk are somewhat horizontal while the lower body is supported at a steeper angle on the wedge which supports the abdomen and lower extremities.

In the broad context the invention may be made from a single structure or it may be constructed from a plurality of separate structures that are placed one on top of the other to conform to the needs of the infant.

Further objects and advantages will be made more apparent by referring now to the accompanying drawings where there is shown:

Figure 1:
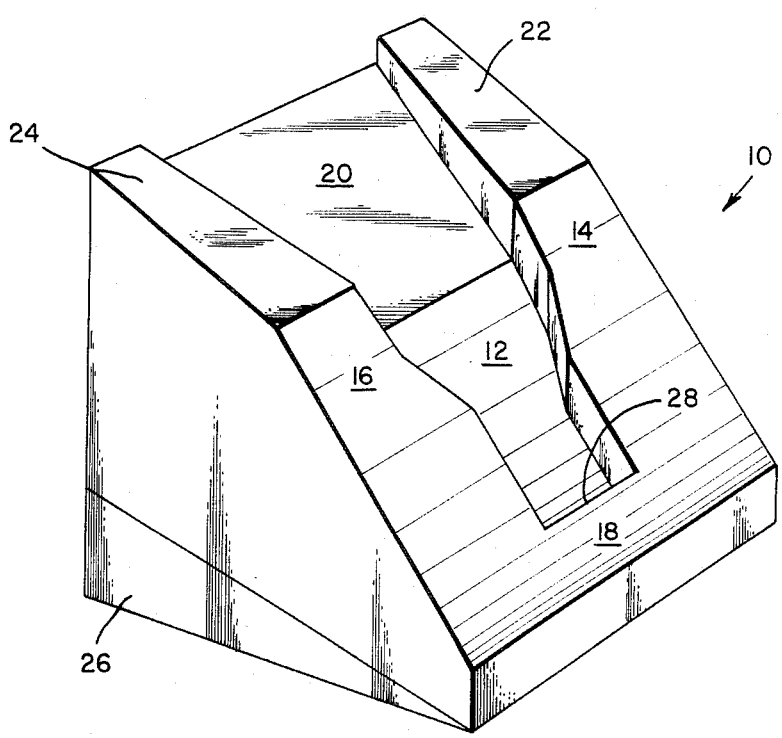
FIG. 1 illustrates an elevated infant positioner constructed of a single foam wedge.

Referring now to FIG. 1, there is shown an elevated infant positioner 10 adapted to support an infant in either a prone or supine position. The positioner 10 is constructed of a single wedge of foam and contains a first flat surface 12 having a given angle that is preferably at least 30 degrees relative to the horizontal.

The foam material that is formed to define the first flat surface 12 forms a pair of extending arms 14 and 16 that are connected together at a base portion 18.

A second flat surface 20 contains an angle that is less than the angle of the first flat surface 12 and is contiguous with the first surface. In the preferred embodiment the extending arms 14 and 16 are each tapered and extend out as arms 22 and 24 and are each in contact with the second flat surface 20.

The complete positioner 10 is adapted to sit on a separate wedge-shaped foam material 26 (illustrated in FIG. 3) having the same base portions as the positioner 10. The angle of the wedge-shaped member 26 is preferably less than 30 degrees and thereby allows the user the option of selecting the ultimate angle of the first flat surface 12 relative to a given horizontal by selecting a wedge 26 of any other suitable angle.

The infant is basically placed on the first inclined surface 12 in either a prone or supine position. Placing the child in the supine position allows the back of the child and the head to be supported by the flat resilient surface 12 while the shoulder portion 28 near base member 18 supports the buttocks of the infant while the extending bifurcated portions 14 and 16 prevent lateral movement of the infant.

The child may also be placed in the prone position by placing the stomach of the child on the flat surface 12 and allowing the head of the infant to be placed on the second flat surface 20. The tapered extended arms 22 and 24 provide the dual functions of preventing lateral movement of the child while at the same time allow additional space for the child to move his hands over his head. The shoulder 28 associated with base portion 18 will also provide a limit to the vertical movement of the child while lying on the first flat surface 12.

Figure 2:
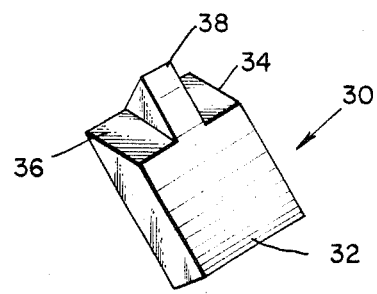
FIG. 2 illustrates a foam insert for repositioning the infant.

Referring now to FIG. 2, there is shown a foam insert 30 that is basically rectangular in shape and is adapted to fit within the lowermost portion of the flat surface 12 illustrated on FIG. 1. Edge 32 is adapted to abut against shoulder 28 thereby placing incline plane 34 and incline plane 36 in a direction facing the infant. Located between the incline planes 34 and 36 is a solid foam projection 38 that is adapted to limit the vertical movement of the child should the child slide down the incline plane 12. The legs of the child will be formed against the incline planes 34 and 36 of wedge 30 thereby cradling the child while at the same time preventing his movement in a vertical direction down plane 12.

The wedge illustrated in FIG. 2 is intended to be used in those situations where the infant is extremely small and it is desired to place the infant in the prone position with its head on the second incline plane 20 illustrated in FIG. 1. Depending on the actual angle selected, it may be necessary to physically prevent the child from sliding down the incline plane 12, which protection will be afforded by the wedge 30 illustrated in FIG. 2.

It will be appreciated by those skilled in the art that regardless of whether the child is located in a prone or supine position, the child is always adequately supported and protected and at the same time movement of the child is not impaired, thereby allowing the child to develop in its normal active manner without undue restraints.

The embodiment illustrated in FIG. 1 is intended to show how the infant positioner may be constructed of a single foam wedge and still perform the functions of allowing a single structure to support the infant in either a prone or supine position.

A second embodiment of the invention is intended to show how the invention may be constructed of a plurality of separate foam sections that perform the same function of FIG. 1 but allow the user some greater latitude in positioning or repositioning the elements to suit his or her personal needs.

Figure 3:
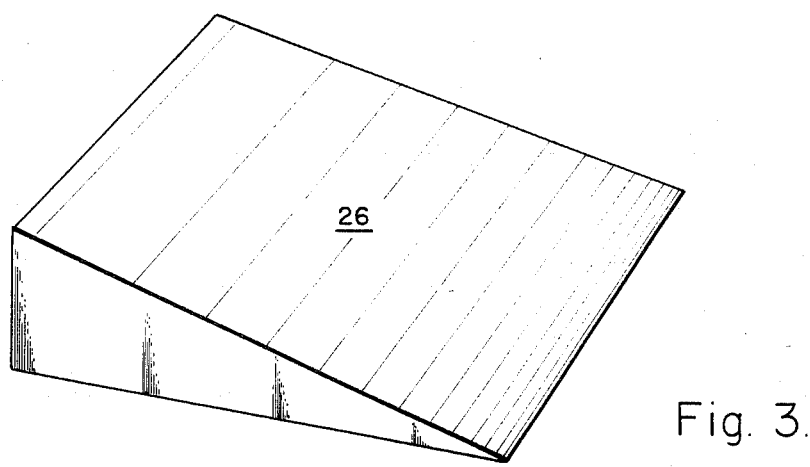
FIG. 3 illustrates a separate foam wedge for changing the angle of the infant positioner.
Figure 4:
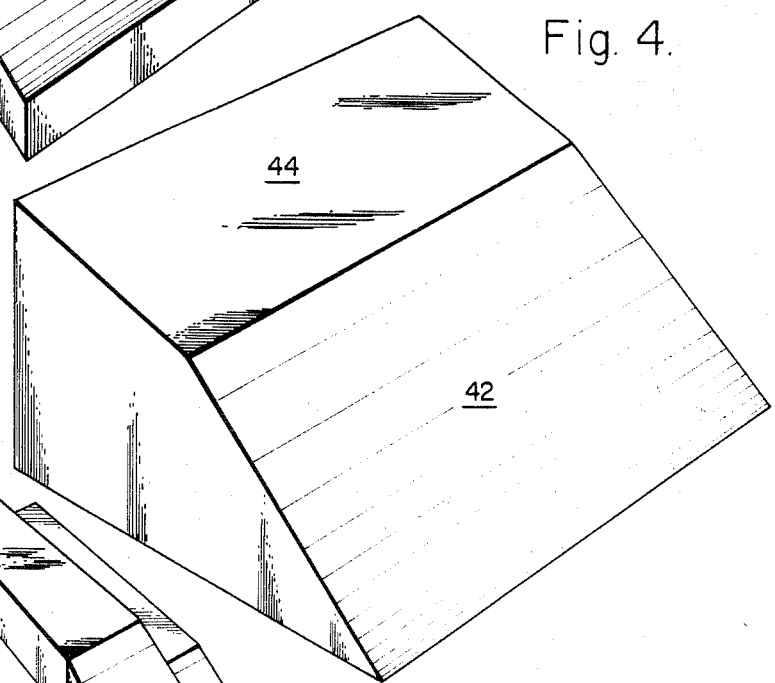
FIG. 4 illustrates a base member of a second embodiment of the infant positioner.

Referring now to FIG. 4, there is shown a base member 40 containing a first incline plane 42 having an angle that is preferably at least 30 degrees with respect to the horizontal and a second contiguous plane 44 having an angle that is less than the angle formed by plane 42. The total angle made by 42 with respect to the horizontal may be changed by utilizing a separate wedge member 26 illustrated in FIG. 3 and described in connection with FIG. 1.

Figure 5:
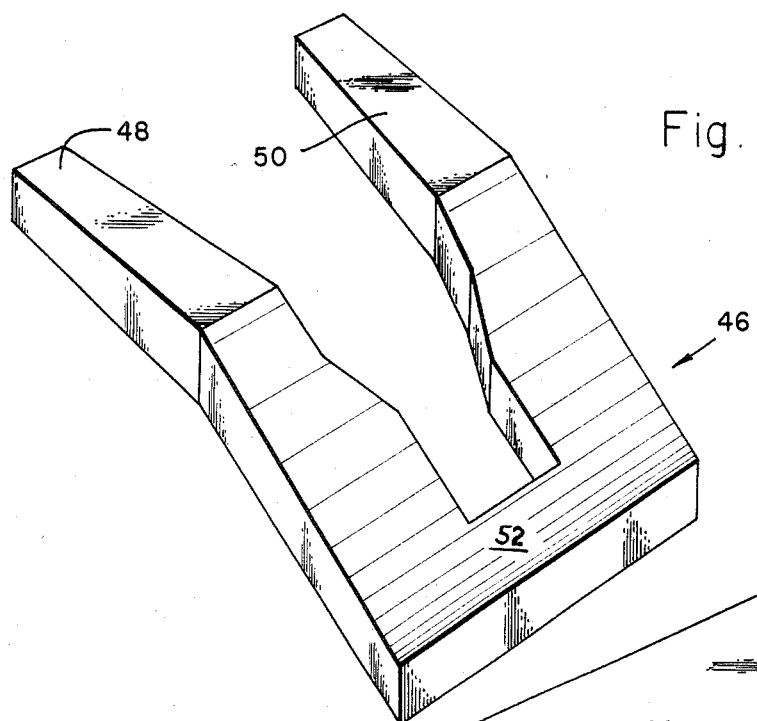
FIG. 5 illustrates a bifurcated foam member for supporting the infant on the wedge and preventing lateral and vertical movement.

Referring now to FIG. 5, there is shown a bifurcated U-shaped member 46 containing a pair of tapered extending arms 48 and 50. Bifurcated member 46 is also constructed of the same foam material used to construct the base member 40 illustrated in FIG. 4 and has a thickness sufficient to restrain the movement of the infant in either a vertical or lateral position.

Figure 6:
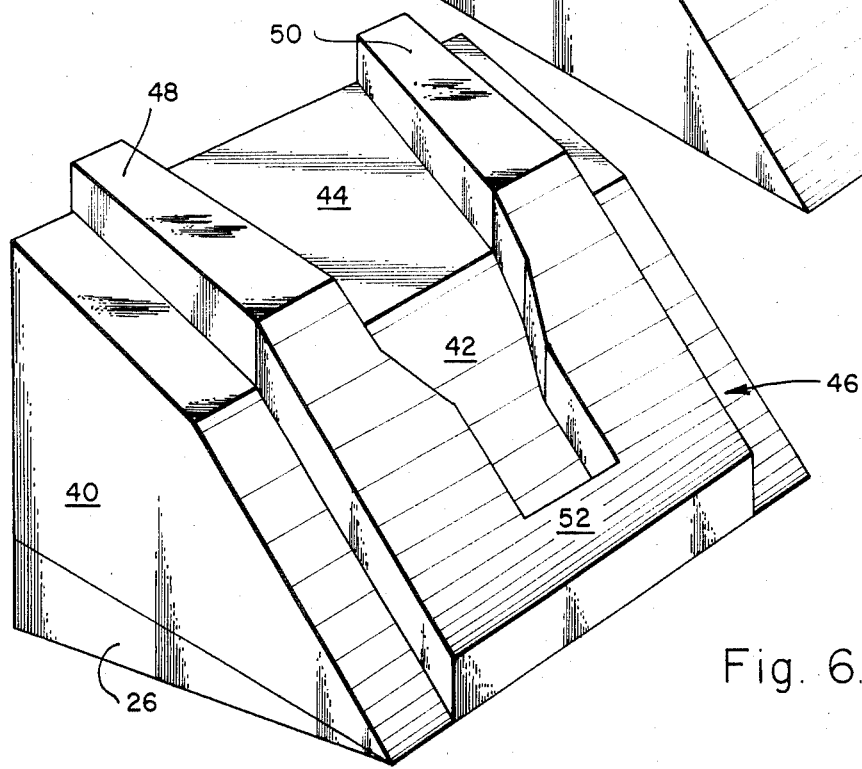
FIG. 6 illustrates the complete assembly of FIGS. 3, 4 and 5.

Referring now to FIG. 6, there is shown the complete assembly of FIGS. 3, 4 and 5 and which illustrate the base member 40 located on wedge 26 of FIG. 3 together with the bifurcated portion 46 located in part on surface 42 and surface 44.

The extending arms 48 and 50 are individually movable in a lateral direction to accommodate the needs of the infant and to allow for the proper movement of the infant when in either the supine or prone position.

It will be apparent to those skilled in the art that different shaped bifurcated U-shaped members 46 may be constructed having a base member 52 that can be larger or smaller depending on the size of the infant and where it is desired to place the infant on either of the surfaces 42 or 44.

I claim:

1. A device for safely holding and supporting an infant in either a prone or supine position at a given angle relative to the horizontal comprising:

a first member in the form of an inclined plane havine a first flat surface at a given angle of substantially 30 degrees and adapted to support an infant, a second bifurcated member having a U-shaped cross-section in contact with said flat surface and having a thickness adapted to prevent vertical and lateral movement of the infant, and said first and second member being contstructed of a resilient foam material having a density for supporting and restraining the infant.

2. A device according to claim 1 in which said bifurcated U-shaped member has a pair of arms in contact with said first flat surface to prevent lateral movement of the infant and a base portion in contact with said first flat surface to prevent vertical movement of the infant.

3. A device according to claim 2 in which said pair of arms are each tapered away from said base portion to provide a larger area for movement of the infant.

4. A device according to claim 2 in which said pair of arms are movable laterally with respect to each other.

5. A device according to claim 1 in which said first member and said second bifurcated member are constructed of a solid unitary structure.

6. A device according to claim 1 which includes a second base member in the form of an incline plane and having an angle that is less than said given angle on said first member and adapted to support said first member thereby changing said given angle with respect to the horizontal.

7. A device according to claim 6 in which said second base member is constructed of the same resilient foam material used to construct said first and second member.

8. A device according to claim 1 which includes a second flat surface contiguous with said first flat surface and at an angle that is less than said first angle.

9. A device according to claim 8 in which said birfurcated U-shaped member includes a pair of arms in contact with said first flat surface and said second flat surface and a base member in contact with said first flat surface.

10. A device for safely holding and supporting an infant in either a prone or supine position at a given angle relative to the horizontal comprising:

a base member in the form of an incline plane having a first flat surface at a given angle of 30 degrees and a second flat surface contiguous with said first surface and at an angle that is less than said first angle whereby the angle of 30 degrees provides the necessary support for the infant in both the supine position and the prone position without the necessity of adding additional parts or members, and a second bifurcated member having a pair of extending arms and a base member, said base member located on said first flat surface and said pair of extending arms located in part on said first flat surface and in part on said second flat surface.

11. A device according to claim 10 which includes a second base member in the form of an inclined plane and having an angle that is less than said given angle on said first member and adapted to support said first base member thereby changing said given angle with respect to the horizontal.

12. A device according to claim 11 in which said base member, said second birurcated member and said second base member are all constructed of the same resilient foam material.

* * * * *